United States Patent
Van Michaels et al.

(10) Patent No.: US 6,582,377 B1
(45) Date of Patent: Jun. 24, 2003

(54) HIGH ACCURACY NON-INTRUSIVE FERTILITY CHOICE DEVICE FOR WOMEN, USING POLARIZED LIGHT

(76) Inventors: Christopher Van Michaels, 1735 N. Hudson Ave., Hollywood, CA (US) 90028; Maria Schneider, 17171 Bolsa Chica Rd., app. 82, Huntington Beach, CA (US) 92649

( * ) Notice: Subject to any disclaimer, the term of this patent is extended or adjusted under 35 U.S.C. 154(b) by 0 days.

(21) Appl. No.: 09/136,943

(22) Filed: Aug. 20, 1998

Related U.S. Application Data

(60) Provisional application No. 60/057,310, filed on Sep. 2, 1997.

(51) Int. Cl.[7] ................................................. A61B 5/00
(52) U.S. Cl. ........................................ 600/551; 359/379
(58) Field of Search .................................. 600/551, 591; 359/379, 385, 390, 801, 804

(56) References Cited

U.S. PATENT DOCUMENTS

| | | | | |
|---|---|---|---|---|
| 4,779,627 A | * | 10/1988 | Kosasky | 600/551 |
| 4,815,835 A | * | 3/1989 | Corona | 600/551 |
| 5,572,370 A | * | 11/1996 | Cho | 600/551 |

* cited by examiner

*Primary Examiner*—Max Hindenburg

(57) ABSTRACT

This invention introduces a high accuracy fertility-no-fertility choice device for women. The device-indicator is based on precise examination of the saliva estrogen and for that purpose is used either linear or circular polarized light, plus quick spectral and contrast analysis. All features of the device are built in a special purpose individual mini microscope.

4 Claims, 3 Drawing Sheets

HIGH ACCURACY NON-INTRUSIVE FERTILITY CHOICE DEVICE FOR WOMEN, USING POLARIZED LIGHT

This application claims priority from Provisional application Ser. No. 60/057,310, filed Sep. 2, 1997.

SUMMARY OF THE INVENTION

The normal menstrual cycle of all women is always modulated by a variety of ovarian steroids and peptides, among which estrogen is the primary regulator. Example: early in the cycle the concentration of the estrogen in the blood is very low, in the order of 20–60 pg/mL, while during the 6 days fertile period (in the middle of the 28 days cycle) it leaps to 200 pg/mL, or up to 10 times. (See FIG. 1(a)) Contrary to that, the variations of the body temperature (which is also modulating the menstrual cycle, see FIG. 1(b), and used by many women to determine the ovulation) changes only in the interval of 37(−0.3+0.5)° C., making the temperature inacurate fertility indicator. Additionally to the above, the estrogen is known to coordinate the systemic response during the ovulatory cycle, including the growth and maintenance of the reproductive tract, pituitary, breasts, and other tissues. Studying the estrogen behavior as above narated, these inventors realized that is possible to engineer a good NON INTRUSIVE FERTILITY-NON FERTILITY DEVICE-INDICATOR FOR WOMEN, using the variations of the estrogen as indicator. Studying further the problem the inventors realized that the best way to perform that task is to employ the linear and the circular polarized light, as well as a quick spectral analysis to detect the estrogen (not in the blood, but) in the saliva. That way these inventors engineered a high accuracy non intrusive fertility choice device, as special object of this invention. Other objects of the invention should become apparent to those skilled in the art,upon reading the disclosure.

REFERENCE TO THE DRAWINGS

DETAILED DESCRIPTION OF THE INVENTION

Studying the steroid skeleton as chemical feedstock for synthesis of anti cancer drugs, inventor VAN MICHAEL, Christopher, opened VOLUME 13 of Kirk Othmer's "ENCYCLOPEDIA OF CHEMICAL TECHNOLOGY" to review the HORMONES, since they are equally derived from the steroides. There, (on page 499, under the sub title PHARMACOLOGICAL EFFECTS) he was struck by the excellent capability of the estrogen as indicator of the fertility-non fertility status during women's menstrual cycles. Independently from him, the co-inventor of this invention, MARIA SCHNEIDER, was looking, (roughly in the same time and in the same encyclopedia) for some of the hormons as promoters of the breast cancer. Hence, she was struck like VAN MICHAELS by the same phenomenon. Since they knew each other, they shared their finding and decided to prepare jointly this patent disclosure, as JOINT INVENTORS. The vast professional literature indicated in the same encyclopedia is (public domain) concerned mainly with synthesis of hormons; their chemistry, pharmacological effects, and not with devices like this one, disclosed in this paper.

Estrogen is not a single compound. It is a family of natural and synthetic varieties, all obtained from modification of the basic steroid skeleton given by the structural formula 1:

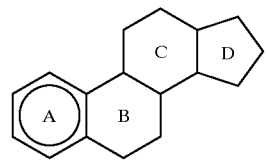

1).

where: A is a phenolic ring, and primary approach in the development of new synthetic estrogens with superior biological profiles; Of course the functional groups in the B, C, and D rings are also subject of modification during the synthesis of the natural or artificial estrogens. As said estrogens are also naturally occurring steroid sex hormones having the ability to induce estrus in all female mammals. More particularly, they are derivatives of the steroid sub group of the planar tetracyclic estra-1,3,5(10)-trien-3-ol shown by formula 2:

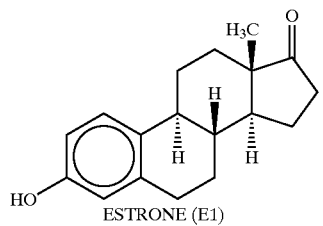

2.1
ESTRONE (E1)

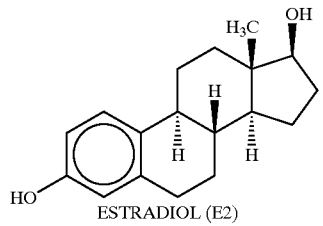

2.2
ESTRADIOL (E2)

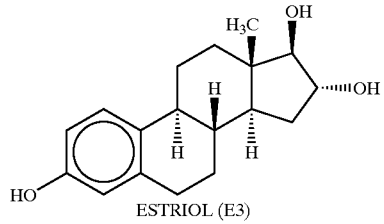

2.3
ESTRIOL (E3)

The principal human estrogens derived naturally from formula 2 are; ESTRONE (E1), ESTRADIOL (E2) and ESTRIOL (E3), shown by formulae 2.1, 2.2 and 2.3 respectively. We are not going to discuss the biochemical and the pharmaceutical properties of the estrogens since they are not relevant to this invention. What is relevant for this invention is that the estrogens are crystal substances when the saliva solution of estrogens is dried on a glass surface they crystallize in frond like pictures similar also to the leafs of a fern, palm, or seaweed.

Figure 3:
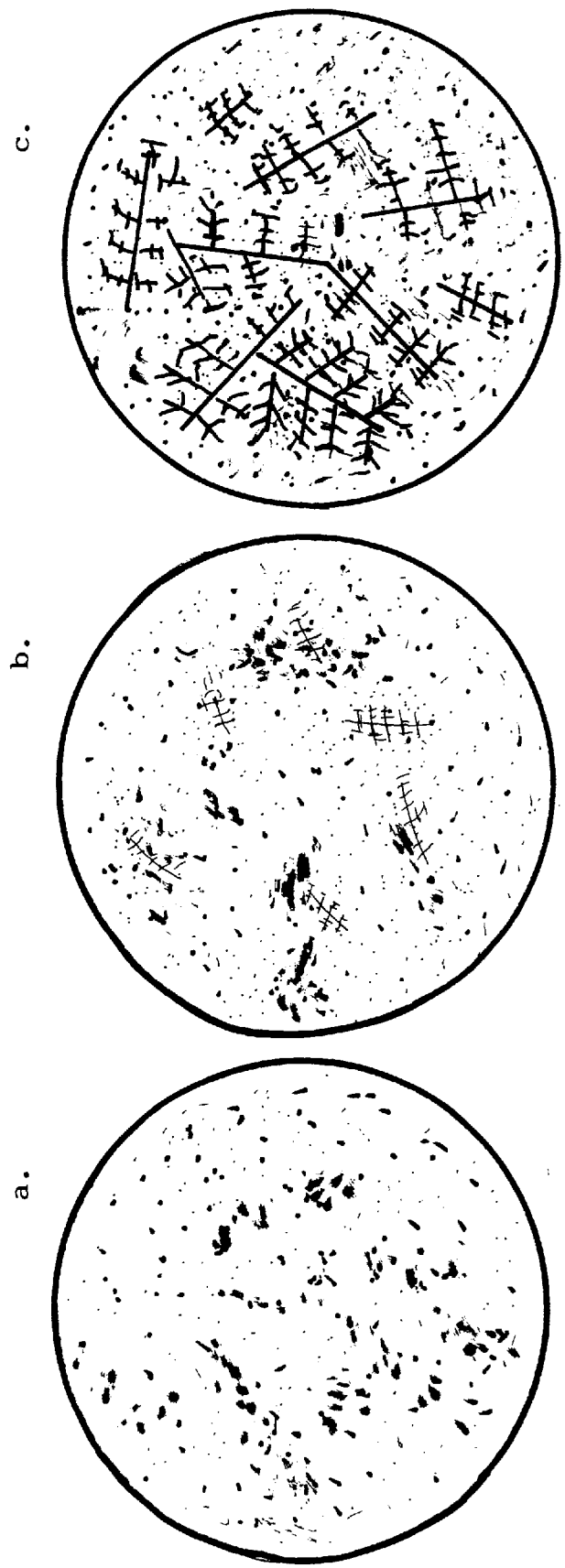
FIGS. 3(a,b,c) represents the usual microscopic pictures of the estrogen in the saliva.

Another relevant matter is that the natural estrogens are produced by the ovaries of the women, mainly during their fertility period (of the menstrual cycle) and that they are readily passing from the blood to the saliva. On the other hand, since the estrogens are also readily metabolized, they exist in the saliva practically only in the fertility period; and to much lower extent in the intermediary period of the menstrual cycle. See FIG. 3(b). Therefore, the particular task of this invention is to accurately detect the presence of estrogens in the saliva during said specific periods, vital for the fertility or no-fertility choice of a family. These inventors found that to do that with unprecedented precision, the women must have, a state of the art, inexpensive, non-intrusive, not harmful, mini "fertility-non-fertility" indicator-device, operated by them selves during the risky days (and nights). Medical laboratories and classic microscopes are not practical for that purpose, since during the critical days and nights, the saliva must be tested for estrogen every 4 to 6 hours. The applicants of this invention solved the problem by invoking for help the linear and the cyclic polarized light obtained and analyzed by suitable polarizers and analysers plus contrast and spectral quick analysis of the polarized light, coming from the estrogen crystals. That is necessary to eliminate the ambiguity of the risky intermediary period, where the estrogen level in the saliva is low. The usual estrogen pictures obtained from the claimed and specialized mini device, are as those shown on FIGS. 3(a,b,c) where: FIG. 3(a) depicts the amorphous infertile period; FIG. 3(b) is the insecure intermediary period displaying barely recognizable tiny frond of estrogen and FIG. 3(c) is a clear fern like picture of the fertile period. To obtain these pictures the device must have a magnifying power of 40× to 80× or more, and be in the mean time inexpensive, reliable and durable.

Figure 2:
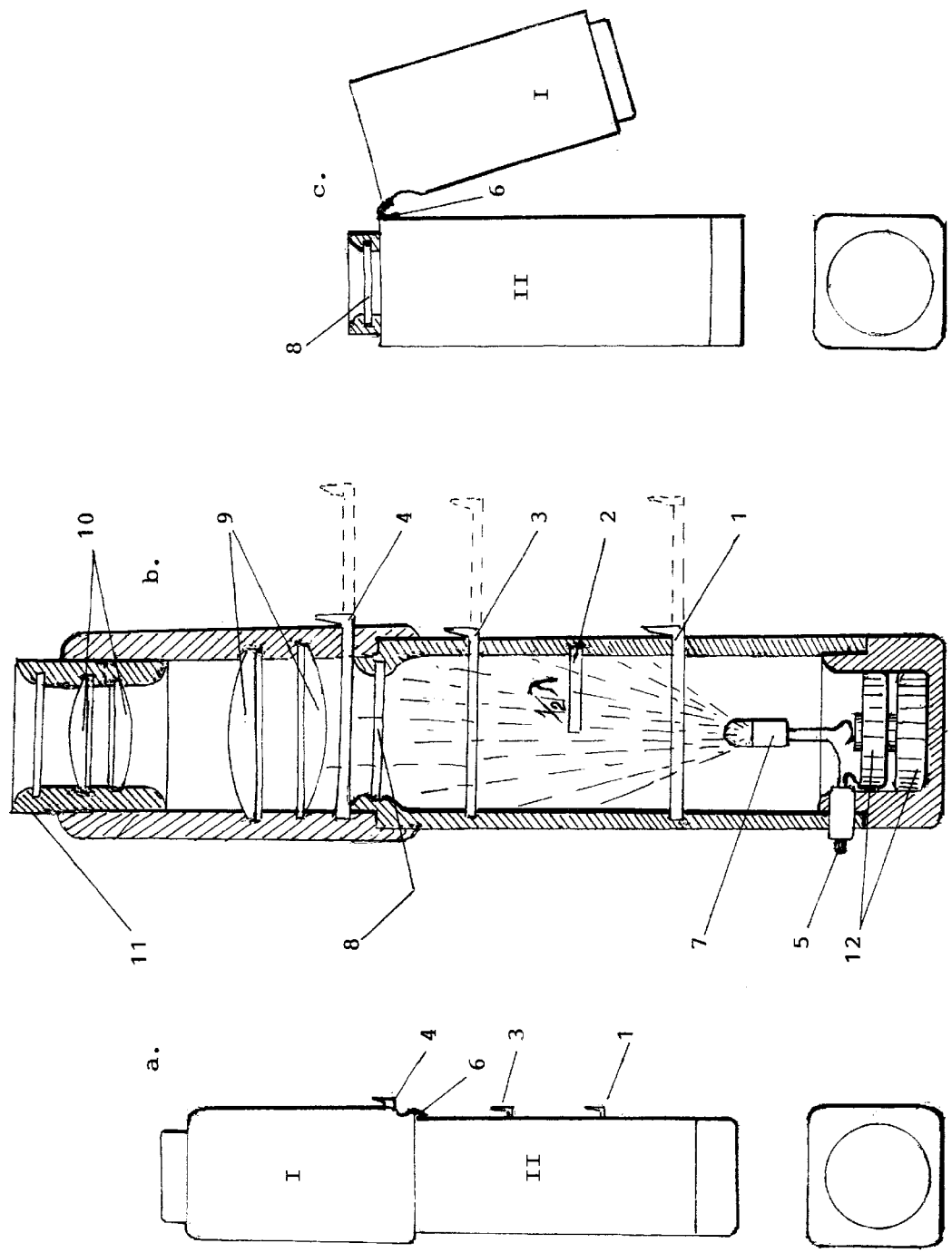
FIGS. 2(a,b,c) is the claimed high accuracy fertility choice device for women.

Obviously the above set of requirements cannot be met by the laboratory microscopes since they cannot be put in a woman's purse and are expensive. On the other hand, miniaturized students microscope equally is not a good solution since the detection of the estrogen during the intermediate period of FIG. 3(b) requires more precision. Consequently, this inventors decided to diversify the mini device by including in its capability also the analysis of the saliva estrogen by polarized light. That feature is explained further in this disclosure. The claimed non intrusive fertility-no fertility choice device is best explained following its construction shown on FIGS. 2(a,b,c). There, FIG. 2(a) represents an outside look of the device where one can seethe knobs of the polarizing filter 1; of the contrast (by optical delaying path) device 2; of the spectral rotating sheet 3, needed for said quick spectral analysis; the knob 4 of the analizing filter and the button 5 of the LED (Light Emitting Detector inside inside the device); on same FIG. 2(a) I depicts the outside view of the analizing mini microscope of the device, and II—is its polarizing illuminator. Detail 6 represents a pair of rubber bands keeping I and II together.

Figure 1:
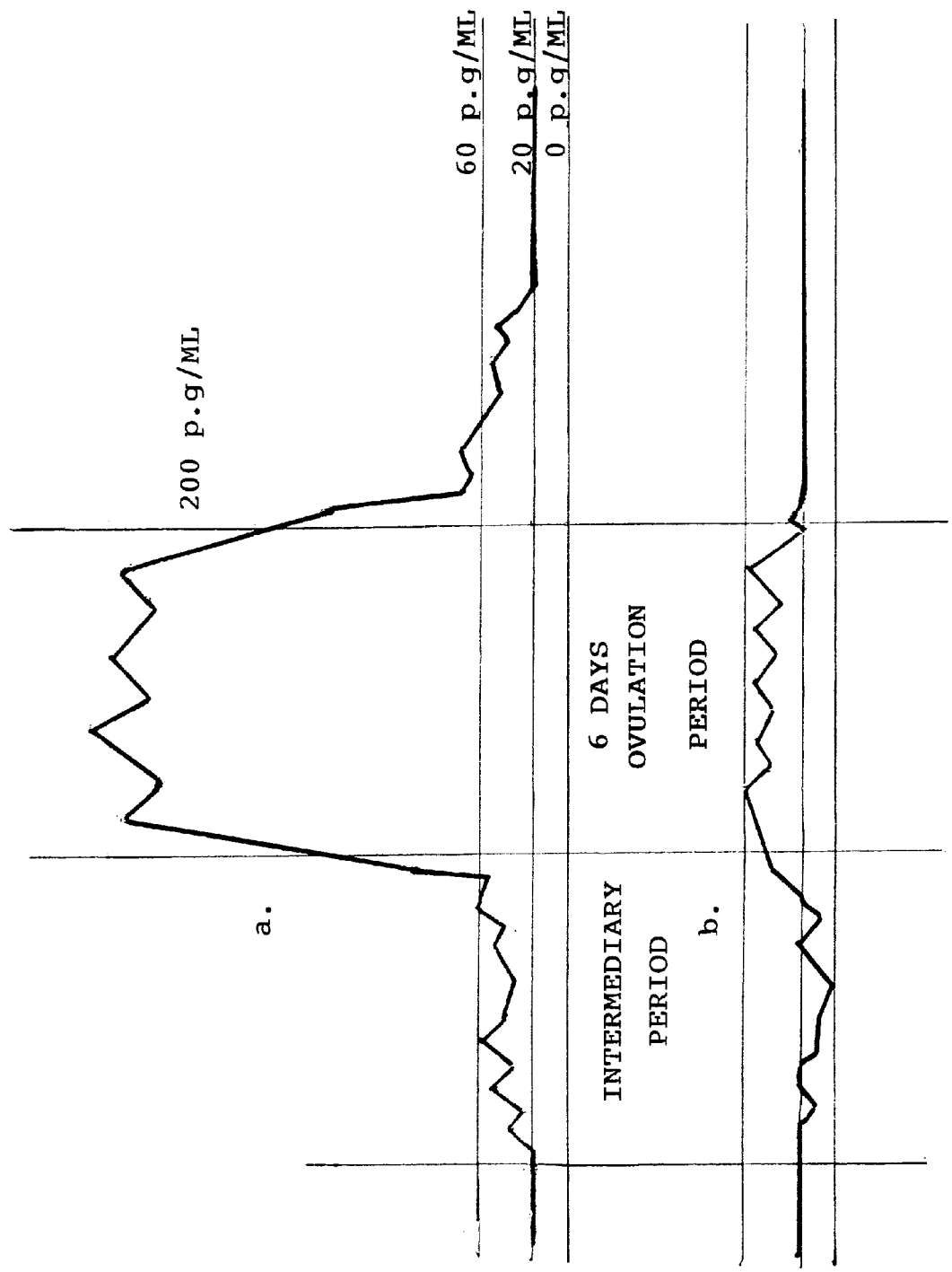
FIGS. 1(a,b) represents the stated variations of the estrogen and the body's temperature during the menstrual cycles of the women.

FIG. 2(b) represents magnified, longitudinal section, of the same device helping to understand, in a better way, its internal construction and advanced action. There, details 1, 2, 3, 4, and 5 are same as those of FIG. 2(a); detail 6 is not shown and the sub devices I and II have the same meanings as above indicated. Detail 7 represents the mentioned LED; device 8 is the glass used to apply and dry the saliva specimen (needed for searching of estrogen); 9 represent the objective lenses; 10 are the eyepiece (ocular) lenses and 11 is (bolt & nut type) fitting needed for adjustment of the ocular to the particular eye of the observer. The so described fertility choice device works as follows:

Hormones show up in the women's saliva only during the 6 days fertility (ovulation) period of women's monthly cycles (rufly between 11 and 17 days). The estrogen is crystalline organic substance dissolved in the blood from where it readily passes in the saliva where it is again in a dissolved state. However, by drying the saliva for 5 to 10 minutes, applyed upon a flat glass surface, it crystallizes quickly into beautiful frond like shapes, especially when has been taken to avoid tiny bubbles in the salive when transferred on the surface of the specimen glass 8. Once that is done, the optical checking for estrogen in the saliva proceeds both by regular and polarized light as follows:

(A) To proceed with regular (non polarized) light the observer must first pull off the polarizing filter 1, the sheet of the spectrum rotation 3 and the analyzer 4. Once that is done, the device works as regular laboratory microscope and the observer could see the frond like picture of the estrogen (showing only during the 6 days fertile period when there is sufficient estrogen in the dried saliva). The beginning of that period is critical information "to have or not to have pregnancy". It is not secure to find out that specific day (and hour) by the way of statistical approach or by measuring the body temperature curve of FIG. 1(a), since women's 28 days cycles are often variable due to cold, flue, stress, inflammation or other illness. On the other hand, the preceding uncertain intermediate period of FIG. 2(b) needs more attention and precision since its last day is the first day (and hour) of the fertile period shown on FIG. 2(c). The same applys to the last day of the fertile period, since after that starts the infertile period. To avoid unwanted mistakes, and feel more comfortable and relaxed, women shall know those days with 100% certainty, including the total actual length, and dates, of the fertility period. To do that our fertility choice device has the following additional features:

(B) the CONTRAST FEATURE, which works both with regular and with polarized light. It is performed by back insertion of the optical velocity delaying plastic plate 2. Since the insertion covers only half of the light coming from the LED source, the normal and the delayed beams interfere and produce more sharpness (contrast) upon the examined specimen;

(C) POLARIZED LIGHT ELIMINATION OF UNWANTED NOT RELEVANT OBJECTS. That feature is attained by back insertion of the polarizing and the analyzing sheets 1 and 4 which could be of linear or of circular kinds. The linear polarizer transmits light whose waves vibrate in one only direction. The analyzer which is purposely mounted between the specimen and the objective, is a second polarizing element (polarizing plastic sheet) with its axis crossed at 90° with respect to the polarizer 1. That means, that the polarizer and the analyzer combine to block out all the light coming from a specimen that does not affect the state of polarization (like the saliva water, transparent bacteria and air bubbles). As a result, the background of the observed picture becomes BLACK. However, the estrogen crystals depolarize the light. As a result, part of the depolarized light passes through the analyzer, making the crystals visible and shining on the black background, revealing details not visible by unpolarized illumination. This important feature of the device is especially valuable in searching estrogen crystals in the saliva during the uncertain (intermediate) period shown on FIG. 2(b), when the dissolved estrogen in the saliva is very low;

(D). THE COLOR FEATURE OBTAINED BY ANGULAR DISPERSION OF THE POLARIZED LIGHT. Many crystals do not reflect all colors of the light in same proportions as found in the light spectrum. As a result they become more or less colored and the contrast by observing them is different in differently colored light. The claimed fertility choice device can conveniently produce all desired colors from a white beam of light the following way: after inserting in the device its elements 1, 2 and 4, one must insert also its element 3, representing a clear nitrocellulose plastic sheet, having the ability to rotate the different color photons of the polarized light at different angles. That creates angular dispersion of the white polarized light. Then, each color can be conveniently and separately observed through the analyzer 4, should the observer rotates the inserted element 3. To do that, the device is provided with extra incision (not shown on the drawing), allowing to rotate the knob of the analyzer 4. That way, the desired contrast could be better than using only element 2.

FIG. 2(*c*) is introduced to display more explicitly which way the device can be used by the women. Evidently, pushing the microscope of the device as shown, uncovers the specimen glass 8. Then, the woman should apply a little saliva with her finger on the glass watching to not make air bubbles. After drying the saliva for 5 to 10 minutes, the microscope must be returned to its original positions shown on FIG. 2(*a*), followed by pushing on the button 5 of the LED. So, the device is ready for examination of the saliva, as above explained with particulars. Detail 12 on FIG. 2(*b*) is the battery of the LED.

Other Novelties:

In order to make the device affordable for all women, beside its classic glass lenses, we are claiming also plastic lenses (of same quality as the glass lenses) for its microscope. On the other hand, to make the device non-pollutant by disposal, its body is projected to be built entirely from bio-degrading plastic materials.

What we claim is:

1. A high accuracy, non intrusive fertility monitor for determining the fertility of women comprising:

a hand held housing having a top and a bottom, a flat optical specimen glass insertable into the top of said housing, an eyepiece located at said top of said housing for viewing the specimen glass, a light source at the bottom of the housing, polarizing elements located between said light source and said specimen glass for polarizing the light before it reaches said specimen glass and consisting of a polarizing filter, an optical delay plate, and a spectral rotating sheet, and an analizing filter between the specimen glass and said eyepiece, wherein the polarized light provides improved optical analysis of estrogen crystals of dried saliva once placed on the specimen glass by making the crystals visible and shining on a black background for better determination of fertility.

2. A monitor like that of claim 1, wherein the polarizing and analyzing filters are of linear polarizing type.

3. A monitor like that of claim 1, wherein said polarizing and analyzing filters are of circular polarizing type.

4. A monitor like that of claim 1, wherein the polarizing and the analyzing filters are eliminated but, the optical delay plate and the spectral rotating sheet are still there and capable of causing contrast view, of the estrogen crystals, with non polarized light.

* * * * *